United States Patent [19]

Neumüller

[11] Patent Number: 5,726,033
[45] Date of Patent: Mar. 10, 1998

[54] PROCESS FOR PREPARING PROTEINS FROM PROTEIN-CONTAINING SUBSTANCE

[75] Inventor: Waldemar Neumüller, Göttingen, Germany

[73] Assignee: Nupron GmbH Proteinwerk, Hardenberg, Germany

[21] Appl. No.: 648,173

[22] PCT Filed: Nov. 22, 1994

[86] PCT No.: PCT/EP94/03857

§ 371 Date: May 17, 1996

§ 102(e) Date: May 17, 1996

[87] PCT Pub. No.: WO95/14394

PCT Pub. Date: Jun. 1, 1995

[30] Foreign Application Priority Data

Nov. 22, 1993 [DE] Germany ............... 43 39 743.3

[51] Int. Cl.⁶ ............... C12P 21/06; A23L 1/32; A23J 1/00; A23J 1/02
[52] U.S. Cl. ............... 435/68.1; 426/614; 426/656; 426/657
[58] Field of Search ............... 435/68.1; 426/656, 426/614, 657

[56] References Cited

U.S. PATENT DOCUMENTS

| | | | |
|---|---|---|---|
| 3,857,966 | 12/1974 | Feldman et al. | 426/7 |
| 4,088,795 | 5/1978 | Goodnight, Jr. et al. | 426/598 |
| 4,265,917 | 5/1981 | Fabre | 426/104 |
| 4,482,574 | 11/1984 | Lee | 426/7 |

*Primary Examiner*—Jon P. Weber
*Attorney, Agent, or Firm*—Thomas, Kayden, Horstemeyer & Risley

[57] ABSTRACT

In a process for preparing proteins from a protein-containing substance, the substance is dispersed in an alkaline solvent with a pH of over 11.5 and at a temperature of under 30° C. The proteins in the substance are thus dissolved. The resulting solution is then neutralized and the proteins in it are concentrated. To improve the profitability of the process in large-scale manufacture, the protein-containing substance is treated with a protease before dispersion in the alkaline solvent.

10 Claims, No Drawings

PROCESS FOR PREPARING PROTEINS FROM PROTEIN-CONTAINING SUBSTANCE

The invention relates to a process for preparing proteins from a protein-containing substance, wherein the substance is dispersed in an alkaline solvent with a pH of over 11.5 and at a temperature of under 30° C., whereby the proteins contained in the substance are dissolved; and wherein the resulting solution is neutralized and the proteins contained in the solution are concentrated. For example, in the production of starch from potatoes, in the production of flour from grain, in the production of tofu and in the production of oil from various plants protein-containing substances are obtained as byproducts, in which the proteins have a structure not directly usable or a structure of low value. In the production of starch from potatoes the protein-containing substance is a denatured, hornificated by drying and insoluble potato protein concentrate. The processing of said potato protein concentrate is particularly difficult, and is, in the following, taken as an example for the preparation of proteins from various protein-containing substances.

A process of the type described above is known from published German Patent Application 41 33 538. Therein, the substance is to be dispersed at room temperature in an alkaline solvent especially having a pH of about 12.5. It is proposed to disperse the substance under homogenization to accelerate the dissolution of the proteins. In this context, it has been found that a ready dissolution in industrial scale applications of the known process can only be achieved with the aid of a homogenization by high pressure disintegration. Long breaking down periods in dissolving the proteins in the alkaline solvent result in alkali damages of the dissolved proteins. The occurrence of alkali damages is also enhanced by high temperatures during dispersion of the protein-containing substance in the alkaline solvent.

Disadvantageously, in the process known from published German Patent Application 41 33 538 for preparing the proteins from the protein-containing substance various chemicals have to be used with a great surplus to enable an, especially continuous, industrial scale application of the process. I. e., the dry matter content in each process step is relatively small, and hence, the specific costs for the various chemicals and the specific energy consumption, for example in concentrating and drying the proteins at the end, are high. The low acceptable dry matter concentration in the continuous application of the process can be put down to the fact that the protein-containing substance as such is hardly dispersable. Therefore, an effective homogenization by means of high pressure disintegration has to take place in bypass. A single high pressure disintegration is not sufficient for homogenization.

Further, the proteins prepared according to the known process are disadvantageously insoluble in the physiological pH range. They have a certain dispersability which, however, depends on the details of the process control. For example proteins concentrated by precipitation and isolated by drying have a dispersability which is high above the protein-containing substance, but which is too low for various applications, for example, for using the proteins as animal food or in the food stuff industry.

A process for preparing proteins from a protein-containing substance, wherein said substance is dispersed in an alkaline solvent with a pH of over 11.5, whereby the proteins contained in the substance are dissolved; and wherein the resulting solution is neutralized and the proteins contained in the solution are concentrated is also known from U.S. Pat. No. 4,624,805. With regard to the protein-containing substance, the process starts with untreated agricultural products, especially with grain. The grain is milled and stirred in the alkaline solvent. The dispersion of grain flour and alkaline solvent is treated with ultrasound to accelerate the dissolution of the proteins which are still native, here. Therein, a maximum temperature of 54° C. is kept. The lowest temperature during dispersion in the alkaline solvent which is reported in the examples of U.S. Pat. No. 4,624,805 is 38° C. At said temperature alkali damages already occur in the prepared proteins. The ultrasonic treatment of the protein-containing substance during dispersion is insufficient for effectively accelerating the dissolution. Additionally, an ultrasonic treatment with a high energy transfer can not be realised on an industrial scale. High dry matter contents are also impossible while continuously carrying out the process known from U.S. Pat. No. 4,624,805. Herein, even the ultrasonic treatment during dispersion of the protein-containing substance in the alkaline solvent is an obstacle.

WO-91/12730 starts from the problem of the industrial applicability of the process described at last. As a solution, a fine milling of the protein-containing, native starting substance is proposed. The fine milling takes place in an attritor after adding water to the grain crushed before. Afterwards, the protein-containing substance is dispersed at about 50° C. in the alkaline for one hour. These conditions are necessary to ensure a sufficient yield of protein. However, at the same time it is inevitable that they lead to alkali damages in the proteins obtained.

In the field of food stuff technology, it is known to treat proteins with proteases for enhancing their physiological solubility, for example from the overview article "Proteases" (Jens Adler-Nissen in "Enzymes in Food Processing" edited by Tilak Nagodawithana, Gerald, Academic Press, San Diego 1993). However, it is found that with the aid of proteases, only, a break-down of the potato protein concentrates obtained in the production of starch is impossible. Additionally, an extensive use of proteases can lead to an undesired bitterness of the proteins made soluble.

It is the object of the invention to further improve a process of the type described at the beginning, so that its, especially continuous, industrial scale application is possible with high dry matter contents. Further, an improvement in product quality of the processed proteins shall be achieved.

According to the invention this is achieved in that the protein-containing substance is treated with a protease before said dispersion in said alkaline solvent having said pH of over 11.5.

Surprisingly, it is found that the initial treatment of the protein-containing substance with the protease is not sufficient for breaking-down the proteins, but that the properties of the protein-containing substance are significantly improved with regard to further processing the proteins. Thus, the dispersability, especially in the alkaline solvent, is strongly increased, whereby the new process allows significantly increased dry matter contents without hindering a continuous procedure. Herewith, the expenses for chemicals and the energy consumption in concentrating the processed proteins are reduced at the same time. The pre-treatment with the protease also leads to a strong improvement in the following dissolution of the proteins in the alkaline solvent. This has the effect that the same yield of protein is obtained within a shorter period of time or by lower technical efforts in the homogenization. Thus, the homogenization by means of high pressure disintegration which was necessary before can be avoided. In certain cases simple stirring of the dispersion can be sufficient. This can be put down to the fact that the proteins in the protein-containing substance are incubated with the protease, whereby the alkaline solvent can attack the proteins more easily. The dissolved proteins have a modified structure compared to proteins only treated with proteases or strong alkali. This can be put down to the stepwise treatment, first with the protease and then with the alkali. The concentrated and isolated proteins show an enhanced dispersability compared to the basic process, but a solubility of the proteins is not directly given since the protease normally is destroyed in the treatment of the starting substance with the alkali, and since the actual dissolution of the proteins is based on the alkali.

For the treatment with the protease the protein-containing substance can be dispersed in an aqueous lye with a pH of up to 10.5, especially of about 9.5, and at a temperature of 30° to 55° C., especially of about 40° C., wherein a protease is used which is active in the pH range adjusted. For example, potato protein can be mixed up with water so that a 12 to 18% dispersion (with regard to the dry matter) is obtained. The exact dry matter concentration is to be tuned to the swelling properties of the potato protein in the following increase of the pH. The temperature of the dispersion is in the order of about 40° C. Afterwards the pH is adjusted to 9.5, and a protease is added the active range of which includes said pH-value. At pH 9.5, for example, the protease Trypsin would be suitable.

The proteins are sufficiently incubated with the protease, if the protein-containing substance is treated with the protease for 15 to 40 min., especially for about 30 min. Therein, the activity of the protease is advantageously between 50 and 200 International Units, especially between 100 and 150 International Units, per 1 g protein substrate. The activity of the protease is also to be tuned to how the dissolved proteins are to be further processed. For example, if a concentration by precipitation is planed, the activity of the protease must not be chosen too high. On the other side, a high activity of the protease leads to an end product which is well dispersable and already partially soluble.

In the new process, a homogenization of the protein-containing substance is not absolutely necessary. However it is advantageous, if the protein-containing substance is dispersed in the alkaline solvent with the pH of over 11.5 for a short time only and under homogenization. So the occurrence of alkali damages can be minimized. Naturally, the homogenization further enables a general acceleration of the process. Here also, the thermal energy introduced by homogenizing is to be extracted again to avoid an increase in temperature in the alkaline dissolution.

The homogenization can be carried out in different ways, also including ultrasonification, milling in a colloid mill and so on. However, the single step high pressure disintegration at more than 120 bar, especially 150 to 180 bar, is to be mentioned as an example for a particularly suited homogenization of the protein-containing substance with the alkaline solvent. In contrast to the basic process no homogenization by means of high pressure disintegration in bypass is necessary.

However, as in the basic process a relative high pH of the alkaline solvent and a low temperature in the dispersion of the protein-containing substance are desirable. Therefore, the protein-containing substance is preferably dispersed in the alkaline solvent with a pH of 12.5 and at a temperature of about 25° C. Said temperature corresponds to room temperature.

It has already been explained that the treatment of the protein-containing substance with the protease preceding the alkaline dissolution mainly causes advantages with regard to the process control and does not directly have the effect of a solubility of the end product. For achieving a solubility of the end product in the physiological range the dissolved proteins can be newly treated with a further protease, especially after at least partial neutralization of the solution. So a solubility of the end product of over 90% in the physiological range can be achieved. A protease treatment which only acts on the already dissolved proteins leads to further increased solubilities of 95% and more. However, the advantages with regard to process control, especially the possibility of a high dry matter content, are not achieved here. For achieving the solubility of the end product by only using of proteases after the alkaline dissolution the protease has to be used with a quite high activity which is already associated with the danger of the occurrence of bitter substances. In the case of proteins already been treated with a protease before the alkaline dissolution an activity of the further protease between 20 and 40 International Units, especially between 25 and 30 International Units, per 1 g protein substrate is sufficient.

The new process is also suitable for processing chicken protein (egg-white) to make it water-soluble. Therefor, the protein-containing substance is to be treated with an additional protease in an aqueous acid before the treatment with the protease in the aqueous lye. By selecting the proteases correspondingly the chicken protein can be transformed into a water-containing gel.

In the following, the invention is explained and described in more detail by means of examples:

EXAMPLE 1

Soluble Potato Protein With Animal Food Quality

Potato protein obtained in the production of starch as a byproduct is milled. Afterwards 5 to 6 g water are added per 1 g potato protein, and the temperature of the dispersion is raised to 37° to 40° C. By means of an 10N lye the pH of the dispersion is raised in a first step to 8.0. Now the alkaline protease from *Aspergillus oryzae* is added with an activity of 30 to 40 I. Units under stirring or any other way of mixing the dispersion. Afterwards the dispersion is held at the adjusted pH under mixing. Therein, the viscosity of the dispersion decreases so that the pH can be adjusted to 9.6 by adding afterwards a further lye. In the following, the protease Trypsin is added with an activity of further 80 to 100 International Units. After the reaction of the protease for 15 to 20 min. at a constant pH, the dispersion is cooled down to room temperature and the pH is raised to 12.5. Then, a homogenization is carried out by means of sonification for 3 to 5 min. depending on the energy introduced, or by means of one passage through a high pressure disintegrator at 150 to 180 bar. Therein, the proteins are dissolved. For a further treatment of the proteins with a protease, Subtilisin Carlsberg is added with an activity of 25 to 30 International Units. Within 5 to 7 min. cracking of the proteins takes place. Therein, keeping of the pH is not necessary. After further 3 min. of stirring the solution is neutralized and the pH is adjusted to 7.5. Thereby, the resulting alkaline period is just 10 min., although the treatment with the second protease takes place in an alkaline milieu. The protein solution adjusted to pH 7.5 is dried. After the last cracking the proteins have a physiological solubility at pH 7 to 8 of over 90%. The obtained proteins are a high-value animal food which is easy to handle.

EXAMPLE 2

Soluble Protein For Food Stuff

Potato protein obtained in the production of starch as a byproduct is extracted with ethanol in a known manner, and afterwards concentrated by means of filtration or centrifugation. The dry matter concentration obtained here is between 40 and 50%. Then, the protein containing substance is mixed up with water until the resulting ethanol concentration is 15% by weight at the maximum. Therein, protein concentrations from 14 to 20% are possible depending on the ethanol content. The obtained dispersion is adjusted to pH 9.5 by means of a 10N lye and to a temperature from 37° to 40° C. under stirring. Afterwards, the protease Trypsin is added with an activity of 150 International Units. While keeping the pH of 9.5 the proteins in the dispersion are incubated with the protease. Therein, the viscosity of the dispersion strongly decreases. After about 30 min. the temperature is lowered under 25° C., and the dispersion is adjusted to a pH of 12.5 by means of a 10N lye. The proteins from the protein-containing substance are dissolved under homogenization of the dispersion by means of high pressure disintegration. The insoluble parts of the substance are separated. Afterwards, the proteins in the solution are precipitated at pH 4.8 by adding acid, and afterwards washed twice with water. The material obtained in this way is mixed up with water, wherein a protein concentration of over 12.5% is adjusted. The pH of the new solution is increased to pH 9.5, and the temperature is adjusted to 37° to 40° C. Afterwards further Trypsin is added with a concentration of 150 International Units. Therein, the dispersed protein is totally dissolved. The obtained solution is split. One part of the solution serves for receiving further precipitated potato protein; the other part is neutralized to pH 7.5 by means of acid and is dried afterwards. After the process getting started, the concentration of the proteins is about 20% already before drying. The physiological solubility of the dried proteins is over 90%.

COMPARATIVE EXAMPLE 1

Soluble Protein For Food Stuff Without Treatment With a Protease Before the Alkaline Dissolution The extracted potato protein having a dry matter content of about 6% is dispersed in an alkaline solvent having a pH of 12.5 and homogenized by means of high pressure disintegration in bypass. Afterwards the insoluble parts of the protein-containing substance are separated; and the dissolved proteins are precipitated by adding acid and separated by centrifugation. In the following, the precipitate is washed twice with water and mixed up with water; and the pH is adjusted to 9.5 as in example 1. The protease Trypsin is added to this dispersion with an activity of about 250 to 300 International Units. The treatment with the protease takes place for 30 min. without keeping the pH. Therein, a pH of about 7.5 is reached automatically so that the proteins can be dried without adding acid. Here, it is also possible to split the protein solution after 15 min for receiving further precipitated material as in example 1. In this way the protein solution can be concentrated to 20% before drying also.

The solubility of the dried protein of 95% is higher than the solubility in example 1. However, the advantages in process controlling while breaking-down the protein-containing substance are not obtained.

It is clear, that in the above examples the protein which is not dissolved before drying may be separated by centrifugation to increase the solubility of the end product up to nearly 100%.

EXAMPLE 3

Soluble Chicken Protein

Dried chicken protein (egg-White) is mixed up and stirred with water at a ratio 1:4. Therein, the formation of foam is to be avoided. The pH of this dispersion is about 6.2. After heating the dispersion to 45° to 50° C. the protease Papain is added with an activity of 50 to 70 International Units per 1 g protein. Afterwards, the dispersion is stirred for 20 minutes at a constant pH. After said period of time the pH is increased to 8.0; and the alkaline protease Subtilisin Carlsberg (*bacillus lichenoformis*) is added with an activity of about 50 International Units per g protein. The proteins are incubated with this protease for further 20 min. After the solution has cooled down to 25° C. the pH is raised above 12. Directly afterwards, the dispersion is homogenized by sonification for 5 min., or once by high pressure disintegration at 180 bar. Directly after the homogenisation the solution is neutralized, and the protease is inactivated according to the manufacturer's instruction. The proteins which are dried afterwards are water soluble.

EXAMPLE 4

Forming of a Stable Protein Gel From Chicken Protein

Chicken protein (egg-white) is at first treated with the protease Papain according to example 3. After increasing the pH to 9 the treatment of the protein-containing substance with the protease Trypsin takes place for 15 min. Therein, the activity of the protease Trypsin is 80 to 100 International Units per g Protein. When increasing the pH to 12.5 afterwards, a spontaneous formation of gel occurs which is further accelerated by homogenization by means of sonification. Therein, 3 to 5 min. sonification period are sufficient. Afterwards, the protein gel can be neutralized and dried, wherein the gel structure is kept.

I claim:

1. A process for preparing proteins from a protein-containing substance, comprising the steps of treating said protein-containing substance with a protease to produce a protease-treated protein-containing substance, dispersing said protease-treated protein-containing substance in an alkaline solvent with a pH of over 11.5 and at a temperature of under 30° C., whereby the proteins contained in the protease-treated substance are dissolved, neutralizing the resulting solution of dissolved proteins and concentrating the dissolved proteins contained in said neutralized solution to obtain a concentrate of dissolved proteins.

2. The process according to claim 1, in which the protein-containing substance is dispersed in an aqueous lye with a pH of up to 10.5, and at a temperature of 30° to 55° C., for the treatment with the protease, wherein a protease is used which is active in the pH range adjusted.

3. The process according to claim 2, in which the protein-containing substance is treated with the protease for 15 to 40 min.

4. The process according to claim 3, in which the activity of the protease is between 50 and 200 International Units (IU), per 1 g protein substrate.

5. The process according to claim 2, in which said process includes the further step of treating said protein-containing substance with a further protease in an aqueous acid before the treatment with said protease in said aqueous lye.

6. The process according to claim 1, further comprising the step of homogenizing the protein containing substance while dispersed in said alkaline solvent having said pH of over 11.5.

7. The process according to claim 6, in which the homogenizing is carried out by means of high pressure disintegration at over 120 bar.

8. The process according to claim 7, in which the protein-containing substance is dispersed in said alkaline solvent having a pH of 12.5, and at a temperature of about 25° C.

9. The process according to claim 8, in which the dissolved proteins from said protein containing substance are newly treated with a further protease.

10. The process according to claim 9, in which the activity of said further protease is between 20 and 40 International Units, per 1 g protein substrate.

* * * * *